US012351604B2

United States Patent
Lu et al.

(10) Patent No.: US 12,351,604 B2
(45) Date of Patent: Jul. 8, 2025

(54) FUSION PROTEIN AND USE THEREOF

(71) Applicants: SHANXI JINBO BIO-PHARMACEUTICAL CO., LTD., Shanxi (CN); FUDAN UNIVERSITY, Shanghai (CN)

(72) Inventors: Lu Lu, Shanghai (CN); Shibo Jiang, Shanghai (CN); Zezhong Liu, Shanghai (CN); Jie Zhou, Shanghai (CN); Qian Wang, Shanghai (CN); Xia Yang, Shanxi (CN); Zhenrui He, Shanxi (CN)

(73) Assignees: SHANXI JINBO BIO-PHARMACEUTICAL CO., LTD., Shanxi (CN); FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 18/865,515

(22) PCT Filed: May 15, 2023

(86) PCT No.: PCT/CN2023/094186
§ 371 (c)(1),
(2) Date: Nov. 13, 2024

(87) PCT Pub. No.: WO2023/217286
PCT Pub. Date: Nov. 16, 2023

(65) Prior Publication Data
US 2025/0163107 A1 May 22, 2025

(30) Foreign Application Priority Data
May 13, 2022 (CN) .......................... 202210522162.6

(51) Int. Cl.
| | |
|---|---|
| *A61K 39/12* | (2006.01) |
| *A61K 39/00* | (2006.01) |
| *A61K 39/145* | (2006.01) |
| *A61K 39/215* | (2006.01) |
| *A61P 31/14* | (2006.01) |
| *A61P 31/16* | (2006.01) |
| *C07K 14/005* | (2006.01) |

(52) U.S. Cl.
CPC .......... *C07K 14/005* (2013.01); *A61K 39/145* (2013.01); *A61K 39/215* (2013.01); *A61P 31/14* (2018.01); *A61P 31/16* (2018.01); *C07K 2319/00* (2013.01); *C12N 2760/16122* (2013.01); *C12N 2760/16134* (2013.01); *C12N 2770/20022* (2013.01); *C12N 2770/20034* (2013.01)

(58) Field of Classification Search
CPC ............ A61K 2039/6031; A61K 39/12; A61K 39/215; A61K 39/145; A61P 31/14
See application file for complete search history.

(56) References Cited

U.S. PATENT DOCUMENTS

2020/0165319 A1    5/2020    Yang

FOREIGN PATENT DOCUMENTS

| CN | 109293783 A | 2/2019 |
|---|---|---|
| CN | 109593126 A | 4/2019 |
| CN | 113234151 A | 8/2021 |
| CN | 113292640 A | 8/2021 |
| CN | 113476593 A | 10/2021 |
| CN | 113817029 A | 12/2021 |
| CN | 113861278 A | 12/2021 |
| CN | 113876938 A | 1/2022 |
| CN | 113980140 A | 1/2022 |
| CN | 114206946 A | 3/2022 |
| WO | 2021160346 A1 | 8/2021 |
| WO | 2021249012 A1 | 12/2021 |
| WO | 2021249013 A1 | 12/2021 |
| WO | 2022079308 A1 | 4/2022 |

OTHER PUBLICATIONS

Wang, Yang et al., "Severe acute respiratory syndrome coronavirus 2 (SARS-CoV-2) cell-in mechanism and spike protein-based vaccine development strategy", Chinese Journal of Cellular and Molecular Immunology, vol. 37, No. 2, pp. 178-184 (Dec. 31, 2021).
McAlinden, A. et al., "α-Helical Coiled-coil Oligomerization Domains Are Almost Ubiquitous in the Collagen Superfamily", The Journal of Biological Chemistry, vol. 278, No. 43, pp. 42200-42207 (Oct. 24, 2003).
Liu, Z., Zhou, J., Xu, W. et al. A novel STING agonist-adjuvanted pan-sarbecovirus vaccine elicits potent and durable neutralizing antibody and T cell responses in mice, rabbits and NHPs. Cell Res 32, 269-287 (2022). https://doi.org/10.1038/s41422-022-00612-2.
Zezhong Liu et al, Applications of the recombinant human collagen type III-based trimerization motif in the design of vaccines to fight against SARS-CoV-2 and influenza virus Synthetic Biology Journal vol. 5, Issue 2.
GenBank DataBase, hemagglutinin [Influenza A virus (A/WSN/1933 (H1N1))] Dec. 29, 2008 GenBank DataBase Accession No. ACF54598.
GenBank UEO84943.1(Jan. 17, 2022).
Fan, Chia-Yu et al., Production of multivalent protein binders using a self-trimerizing collagen-like peptide scaffold, The FASEB Journal 22(11):3749-4032(Nov. 2008).

*Primary Examiner* — Barry A Chestnut
(74) *Attorney, Agent, or Firm* — Lando & Anastasi, LLP (57) ABSTRACT

Provided are a fusion protein and use thereof. Provided is a fusion protein, comprising a trimerization block and an immunogenic block which are connected by a linker, wherein the trimerization block comprises one or more of repeat units set forth in SEQ ID NO. 1; the immunogenic block is an immunogenic protein of a pathogen, for example, being selected from a coronavirus RBD block, an HIV membrane protein or an influenza virus hemagglutinin protein, and immunogenic fragments thereof. Compared with an immunogen monomer, the trimer can generate a higher neutralizing antibody level, does not induce a strong antibody against the trimerization block in a human body, and can promote the immune response of the organism to be focused on the immunogenic block.

13 Claims, 6 Drawing Sheets
Specification includes a Sequence Listing.

Fig.7 titers of neutralizing antibodies to SARS-CoV-2 pseudovirus

Fig.8

H1N1 HA1 specific IgG

- HA1-collagen+CF501
- HA1+CF501

FUSION PROTEIN AND USE THEREOF

CROSS REFERENCE TO RELATED APPLICATIONS

This application is a U.S. National Phase Application of International Application No. PCT/CN2023/094186, filed May 15, 2023, which claims priority to Chinese Patent Application No. 202210522162.6, entitled "A fusion protein and use thereof", filed May 13, 2022, each of which is incorporated herein by reference in its entirety.

SEQUENCE LISTING

The instant application contains a Sequence Listing which has been submitted electronically in XML file format and is hereby incorporated by reference in its entirety. Said XML copy, created on Nov. 1, 2024, is named C23W400801US and is 17,813 bytes in size.

TECHNICAL FIELD

The present disclosure relates to the field of biomedicine technology, and in particular to a fusion protein used as a vaccine.

BACKGROUND OF THE INVENTION

The global pandemic of the novel coronavirus (SARS-COV-2) has resulted in nearly 500 million people infected and more than 6 million deaths. The spike protein(S) of SARS-COV-2 is responsible for recognizing and invading cells, in which the receptor binding domain (RBD) contained in the S protein is the most important, and is responsible for recognizing and binding to the angiotensin (ACE2) receptor to mediate virus entry into cells. The currently developed COVID-19 mRNA vaccines, protein subunit vaccines, and adenovirus vector vaccines are all developed for the S protein or RBD protein of SARS-COV-2. The S protein of SARS-COV-2 is a trimeric protein in its natural state. Many current studies have proven that S protein trimers or RBD protein trimers are more immunogenic than S protein monomers or RBD protein monomers. In order to realize the expression of trimeric proteins of RBD or S protein, some studies have fused Foldon tags to RBD or S protein for expression and formed a trimer form under the effect of Foldon. However, Foldon has a larger molecular weight and its immunogenicity is very strong. Immunizing the human body with a trimer with Foldon fused to RBD/S proteins will produce a strong immune response to the Foldon protein, weakening the antigenic response to SARS-COV-2 S or RBD. Likewise, trimers formed using other non-human tags or materials still have similar shortcomings.

Therefore, other strategies still need to be developed to promote the formation of trimers of immunogens, especially antigens from the novel coronavirus.

SUMMARY OF THE INVENTION

The inventor previously screened and optimized a type III collagen sequence. The recombinant human collagen produced has very good hydrophilicity and stability, its amino acid composition is 100% identical to the corresponding part of the amino acid sequence of natural collagen. It will not produce an immune response when applied to the human body. Furthermore, the recombinant human collagen has a trimer structure and can be widely used in biomedicine and other industries. Since the human type III collagen is an optimized human collagen peptide repeat, expression of its fusion to the RBD protein from the novel coronavirus or hemagglutinin from influenza virus may destroy the trimer structure of the collagen. Furthermore, even if the RBD protein from the novel coronavirus or hemagglutinin from the influenza virus does not destroy the trimer structure of collagen and forms a trimeric protein of RBD, under the influence of this collagen, the trimeric RBD may also have a different structure from the natural RBD trimer, so that an immune response in body cannot be well induced. Therefore, the effect of a fusion of the type III collagen to RBD protein of the novel coronavirus or hemagglutinin of influenza virus as a vaccine is unpredictable. In the present disclosure, the inventor introduced cysteine into the C-terminus of the recombinant human type III collagen to form a disulfide bond to stabilize the collagen. An amino acid linker is designed to fuse with the RBD protein of the novel coronavirus or the hemagglutinin of influenza virus and the fusion is expressed through a eukaryotic system or a prokaryotic system. Finally, the trimeric fusion protein was successfully expressed. Using this recombinant human type III collagen-RBD trimeric protein as a vaccine to immunize mice can produce more potent binding antibodies and neutralizing antibodies than the RBD protein of SARS-COV-2 or influenza virus hemagglutinin monomer. Therefore, the disclosure cleverly fuses the human type III collagen peptide to the RBD protein of the novel coronavirus or influenza virus hemagglutinin in tandem to be expressed, prompting the RBD protein or influenza virus hemagglutinin to form a correct trimer conformation, enhancing the immunogenicity of RBD or influenza virus hemagglutinin. Furthermore, because the human type III collagen sequence comes from humans, it will not induce an immune response in the human body, prompting the immune response specific to the trimer region of the RBD or influenza virus hemagglutinin.

In one aspect, the disclosure provides a fusion protein comprising a trimerization region and an immunogenic region linked by a linker, wherein the trimerization region includes one or more repeating unit(s) wherein the repeating unit is set forth in SEQ ID NO. 1 or has 90%, 91%, 92%, 93%, 94%, 95%, 96%, 97%, 98% or 99% identity to the repeating unit as set forth in SEQ ID NO. 1, provided that the repeating unit retains trimerization function.

In one embodiment, the immunogenic region is an immunogenic protein of the pathogen.

In one embodiment, the pathogen is a virus, bacterium, fungus and/or parasite.

In one embodiment, the immunogenic region is selected from the group consisting of an RBD region of a coronavirus, a membrane protein of HIV, or a hemagglutinin protein of an influenza virus (e.g., H1N1 HA1 protein) and immunogenic fragments thereof.

In one embodiment, the trimerization region contains 10-20 (e.g., 11, 12, 13, 14, 15, 16, 17, 18 or 19) repeating units wherein the repeating unit is set forth in SEQ ID NO. 1 or has 90%, 91%, 92%, 93%, 94%, 95%, 96%, 97%, 98% or 99% identity to the repeating unit as set forth in SEQ ID NO. 1. In one embodiment, the trimerization region comprises one or more regions at the C-terminus or sequences, wherein the region is set forth in SEQ ID NO. 2 or has 90%, 91%, 92%, 93%, 94%, 95%, 96%, 97%, 98% or 99% identity to the sequence as set forth in SEQ ID NO. 2.

In one embodiment, the trimerization region comprises the amino acid sequence as set forth in SEQ ID NO. 3 or a sequence having 90%, 91%, 92%, 93%, 94%, 95%, 96%, 97%, 98% or 99% identity to the sequence as set forth in SEQ ID NO. 3.

In one embodiment, the trimerization region comprises the amino acid sequence as set forth in SEQ ID NO. 4 or SEQ ID NO. 10 or a sequence having 90%, 91%, 92%, 93%, 94%, 95%, 96%, 97%, 98% or 99% identity to the sequence as set forth in SEQ ID NO. 4 or SEQ ID NO. 10.

In one embodiment, the linker is (GGGS)n or (GGGGS)n or (G)n. In one embodiment, n is an integer from 1 to 10. Preferably, the linker is (GGGS)n or (GGGGS)n.

In one embodiment, the trimerization region and the immunogenicity region are at the N-terminus and C-terminus of the fusion protein, respectively.

In one embodiment, the fusion protein comprises the amino acid sequence as set forth in SEQ ID NO. 5 or 9 or a sequence having 90%, 91%, 92%, 93%, 94%, 95%, 96%, 97%, 98% or 99% identity to the sequence as set forth in SEQ ID NO. 5 or 9.

In one aspect, the disclosure provides a nucleic acid comprising nucleotides encoding the fusion protein described herein. In one embodiment, the nucleic acid comprises the amino acid sequence as set forth in SEQ ID NO. 7. In one embodiment, the nucleic acid further comprises the coding sequence of a purification tag, such as a His tag, a GST tag, an MBP tag, a SUMO tag, or a NusA tag. In one embodiment, the purification tag is at the C-terminus of the fusion protein. In one embodiment, the nucleic acid further comprises nucleotides encoding a leader sequence.

In one aspect, the disclosure provides a vector comprising the nucleic acid described herein. In one embodiment, the vector contains expression control elements operably linked to the nucleic acid. In one embodiment, the expression control elements are promoters, terminators, and/or enhancers.

In one aspect, the disclosure provides a host cell comprising the nucleic acid or vector described herein. In one embodiment, the host cell is a plant cell that is unable to regenerate a plant or is not a plant cell. In one embodiment, the host cell is a eukaryotic or prokaryotic cell. In one embodiment, the eukaryotic cell is a yeast cell, an animal cell, and/or an insect cell. In one embodiment, the prokaryotic cell is an *E. coli* cell.

In one aspect, the disclosure provides a trimeric fusion protein comprising the fusion protein described herein.

In one aspect, the disclosure provides a method of producing the fusion protein or the trimeric fusion protein as described herein, comprising:

(1) cultivating the host cells described herein under appropriate culture conditions;

(2) harvesting the host cells and/or culture medium containing the fusion protein or trimeric fusion protein; and (3) purifying the fusion protein or trimeric fusion protein.

In one embodiment, the fusion protein or trimeric fusion protein may be purified from the culture medium. In another embodiment, the fusion protein or trimeric fusion protein may be obtained by homogenizing the host cells and then purifying fusion protein or trimeric fusion protein from the cell lysate.

In one aspect, the disclosure provides compositions comprising the fusion protein, nucleic acid, vector, host cell, and/or trimeric fusion protein as described herein.

In one embodiment, the composition is a pharmaceutical composition. In one embodiment, the pharmaceutical composition is a vaccine. In one embodiment, the composition further comprises pharmaceutically acceptable carriers, excipients, diluents and/or adjuvants. In one embodiment, the adjuvants are aluminum adjuvants, saponin adjuvants, lipid A, monophosphoryl lipid A, trehalose dimycolate, oil emulsion adjuvants, polysaccharide adjuvants, Toll-like receptor activators and/or STING agonists. For example, the adjuvant is In one aspect, the disclosure provides the use of the fusion protein, nucleic acid, vector, host cell trimeric fusion protein, and/or composition described herein in the manufacture of a medicament for the treatment or prevention of pathogen-mediated condition or disease. In one embodiment, the pathogen is a virus, bacterium, fungus and/or parasite. In one embodiment, the virus is selected from the group consisting of coronavirus, HIV, and influenza virus. In one embodiment, the coronavirus is SARS-COV-2. In one embodiment, the influenza virus is an influenza A virus or an influenza B virus.

In one aspect, the disclosure provides a method of vaccinating a subject, comprising administering to the subject the fusion protein, trimer or pharmaceutical composition of the present disclosure.

Compared with the prior art, the beneficial effects of the present disclosure include:

1. The inventor discovered for the first time that by introducing disulfide bonds and linker molecules, the trimerization sequence of the type III collagen can still exert the trimerization function after being fused to the RBD protein of a novel coronavirus or influenza virus hemagglutinin, and the resulting trimers of the RBD or influenza virus hemagglutinin have the correct conformation, producing higher levels of neutralizing antibodies than RBD or influenza virus hemagglutinin monomers.

2. Since the type III collagen is homologous to humans, it will not induce strong antibodies against this collagen, which can prompt the immune response specific to the RBD protein of novel coronavirus or influenza virus hemagglutinin in vivo.

3. The present disclosure also provides a strategy for forming trimers for other immunogens.

DETAILED DESCRIPTION OF THE INVENTION

In order to make the purpose, technical solutions and advantages of the present disclosure more clear, the technical solutions in the examples of the present disclosure will be clearly and completely described below in conjunction with the examples of the present disclosure. Obviously, the described examples are part of the embodiments of the present disclosure, not all the embodiments of the present disclosure. Based on the examples of the present disclosure, all other embodiments obtained by those of ordinary skill in the art without creative efforts fall within the scope of protection of the present disclosure.

As used herein, the inventors used a previously discovered recombinant type III humanized collagen polypeptide as part of a fusion protein to serve as the trimerization domain. In the field of proteins, the structure and/or function of a protein depends to a certain extent on the amino acid sequence. Before the present disclosure, the inventor assumes that adding amino acid residues to one end of the recombinant type III humanized collagen polypeptide may affect the trimerization function of the recombinant type III humanized collagen. Surprisingly, when the recombinant type III humanized collagen is fused with an immunogenic peptide, it is completely able to form a trimerized fusion protein, and the trimerized fusion protein produces significantly improved immunogenicity. For example, in the Examples, the inventors demonstrated that when the recombinant type III humanized collagen forms a fusion protein with the RBD protein of SARS-COV-2 or influenza virus hemagglutinin, trimers can be formed. When compared to the RBD protein of SARS-COV-2 or the RBD protein of SARS-COV-2 or influenza virus hemagglutinin and adjuvant, this trimer, alone or in combination with adjuvants, can produce significantly improved immunogenicity and generate a higher titer of neutralizing antibodies in vivo.

As used herein, a fusion protein refers to a protein formed by linking two or more functional protein moieties indirectly through a linker in frame. A fusion protein may contain a trimerization region, an immunogenic region, and an optional linker. The position of each moiety is not particularly limited. For example, the trimerization region may be at the N-terminus or C-terminus of the fusion protein, and the immunogenic region may be at the C-terminus or N-terminus of the fusion protein.

As used herein, a trimerization region refers to a functional region that can realize a trimerization function. The trimerization region may contain one or more repeating units as set forth in SEQ ID NO. 1. Each of the repeating units may be directly linked or separated by one or more amino acid residues. The number of repeating units may vary. For example, the number of the repeating units may be 2-50, such as 3, 4, 5, 6, 7, 8, 9, 10, 11, 12, 13, 14, 15, 16, 17, 18, 19, 20, 25, 30, 35 or 40. The trimerization region may include one or more stabilization regions as set forth in SEQ ID NO. 2 at the C-terminus. The trimerization region may comprise the amino acid sequence as set forth in SEQ ID NO. 3.

As used herein, an immunogenic region refers to a protein or a fragment thereof (e.g., a fragment of an antigen) derived from a pathogen capable of eliciting an immune response in an organism, in particular a mammal, such as a human body. The immunogenic protein may be selected from the group consisting of a RBD region of a coronavirus, a HIV membrane protein (e.g., gp140) or an influenza virus hemagglutinin protein and immunogenic fragments thereof. The immunogenic region may comprise the amino acid sequence as set forth in SEQ ID NO. 4 or 10. Several prior art documents (such as CN202110676901.2 and CN202111337048.8) disclose a RBD region of a coronavirus and related immunogenic fragments.

The trimerization region and the immunogenicity region may be linked indirectly through a linker. The type of the linker may not be particularly limited. The linker may be (GGGS)n or (GGGGS)n or (G)n. For example, n may be an integer from 1 to 10, such as 2, 3, 4, 5, 6, 7, 8, or 9. Preferably, the linker may be (GGGS)n or (GGGGS)n, thereby a disulfide bond may be introduced.

In order to facilitate the production and purification of the fusion proteins herein, additional moieties may be added to the N-terminus or C-terminus of the fusion proteins of the disclosure. For example, the fusion protein of the present disclosure may contain a secretion signal or leader region at the N-terminus to facilitate secretion of the fusion protein into the culture medium. The fusion protein of the present disclosure may also contain a purification tag at the C-terminus, such as a His tag, a GST tag, a MBP tag, a SUMO tag or a NusA tag to facilitate the purification of the fusion protein. For example, the fusion protein may comprise the amino acid sequence as set forth in SEQ ID NO. 6.

As used herein, nucleic acids include polynucleotides encoding proteins. The nucleic acid may be a native nucleic acid of each moiety of the fusion protein, or may be a codon-optimized nucleic acid to facilitate expression in the target host. The nucleic acid may comprise the sequence of SEQ ID NO. 7.

As used herein, the term "vector" is a nucleic acid delivery vehicle into which a polynucleotide may be inserted. When the vector may express the protein encoded by the inserted polynucleotide, the vector is called an expression vector. The vector may be introduced into the host cell through transformation, transduction or transfection, so that the genetic material elements it carries may be expressed in the host cell. Vectors are well known to those skilled in the art, including but not limited to: plasmids;

phagemids; cosmids; artificial chromosomes, such as yeast artificial chromosomes (YAC), bacterial artificial chromosomes (BAC) or P1-derived artificial chromosomes (PAC); phages such as lambda phage or M13 phage and animal viruses, etc. The vectors may contain a variety of expression control elements, including but not limited to promoter sequences, transcription initiation sequences, enhancer sequences, selection elements and reporter genes. In addition, the vectors may also contain replication origin sites. The vectors may contain nucleic acids of the disclosure for ease of introduction into cells for expression. The vectors may contain expression control elements, such as promoters, terminators and/or enhancers, operably linked to the nucleic acid.

The term "host cell" is a cell into which nucleic acid molecules have been introduced by molecular biology techniques. These techniques include transfection with viral vectors, transformation with plasmid vectors, and introduction of naked DNA via electroporation, lipofection, and bombardment of particle guns. The host cell may be a eukaryotic cell or a prokaryotic cell. The eukaryotic cells are, for example, yeast cells, animal cells and/or insect cells. The prokaryotic cell may be an *E. coli* cell.

The term "subject" refers to any human or other animals, especially other mammals, who are subjected to prophylaxis, treatment, or diagnosis. Other mammals may include, for example, dogs, cats, cattle, horses, sheep, pigs, goats, rabbits, rats, guinea pigs, mice, and the like.

The term "vaccine" as used herein refers to a suspension or solution of an antigenic part, usually containing an infectious agent or parts of an infectious agent, which is injected into the body to produce immunity. The antigenic part for preparing the vaccine may be a microorganism, or a natural product purified from a microorganism, a synthetic product, or a genetically engineered protein, peptide, polysaccharide or similar product. The vaccine herein may be an oral or parenteral vaccine, for example a vaccine administered subcutaneously, intradermally, intravenously, intramuscularly, intraarterially or by infusion.

The term "adjuvant" refers to any substance that increases or modifies the immune response in mixture with an immunogen to be injected. The adjuvant may be aluminum adjuvant, saponin adjuvant, lipid A, monophosphoryl lipid A, trehalose dimycolate, oil emulsion adjuvant, polysaccharide adjuvant, Toll-like receptor activator and/or STING agonist.

The fusion protein of the present disclosure may be assembled into a trimeric fusion protein due to the presence of a trimerization region. The trimeric fusion protein may be a homotrimer or a heterotrimer. Preferably, the trimeric fusion protein is a homotrimer. The trimeric fusion protein of the present disclosure may generate a higher level of neutralizing antibodies than the immunogen alone while lacking immunogenicity against the trimerization region. The fusion protein or trimeric fusion protein of the present disclosure may be produced by the following method, which includes: (1) cultivating the host cell according to the present disclosure under appropriate culture conditions; (2) harvesting the host cells and/or culture medium containing the fusion protein or trimeric fusion protein; and (3) purifying the fusion protein or trimeric fusion protein. There are no particular limitations on the culture and purification conditions, and those skilled in the art can select appropriate culture and purification conditions for isolation of the fusion protein or trimeric protein of the present disclosure.

The fusion protein, nucleic acid, vector, host cell and/or trimeric fusion protein of the disclosure may be prepared into compositions. The composition may comprise the fusion protein, nucleic acid, vector, host cell and/or trimeric fusion protein of the disclosure. For example, the composition may be a pharmaceutical composition, especially a vaccine. In this case, the composition may further comprise pharmaceutically acceptable carriers, excipients, diluents and/or adjuvants. For example, in the case of a vaccine, the vaccine may further contain an aluminum adjuvant, a saponin adjuvant, a lipid A, a monophosphoryl lipid A, a trehalose dimycolate, an oil emulsion adjuvant, a polysaccharide adjuvant, a Toll-like receptor activator and/or a STING agonist, to enhance the immune response of a subject to the immunogen. The fusion protein, nucleic acid, vector, host cell and/or trimeric fusion protein or composition of the disclosure may be used to treat or prevent conditions or diseases mediated by pathogens. Pathogens are viruses, bacteria, fungi and/or parasites. For example, the viruses may be selected from various types of coronavirus, HIV, and influenza viruses. For example, the fusion protein of the present disclosure may be prepared into a vaccine and used to prepare a vaccine for the currently circulating SARS-COV-2 virus or influenza virus.

EXAMPLES

The object, technical features and beneficial effects of the present disclosure will be described in further detail below with reference to the examples, but the implementation of the present disclosure is not limited thereto.

Example 1: Construction and Expression of a Recombinant Human-Derived Type III Collagen-RBD Trimeric Protein The amino acid sequence of the human-derived recombinant type III collagen designed by the inventor is as set forth in SEQ ID NO. 3. The amino acid sequence of the RBD protein of SARS-COV-2 is as set forth in SEQ ID NO. 4. The amino acid sequence of the linker arm therebetween is as set forth in SEQ ID NO. 8. The amino acid sequence of the fusion protein, collagen-RBD protein is as set forth in SEQ ID NO. 6. The optimized nucleotide sequence encoding the fusion protein collagen-RBD protein is as set forth in SEQ ID NO. 7, to which 8 histidine-coding nucleotides and a stop codon are added.

Figure 1:
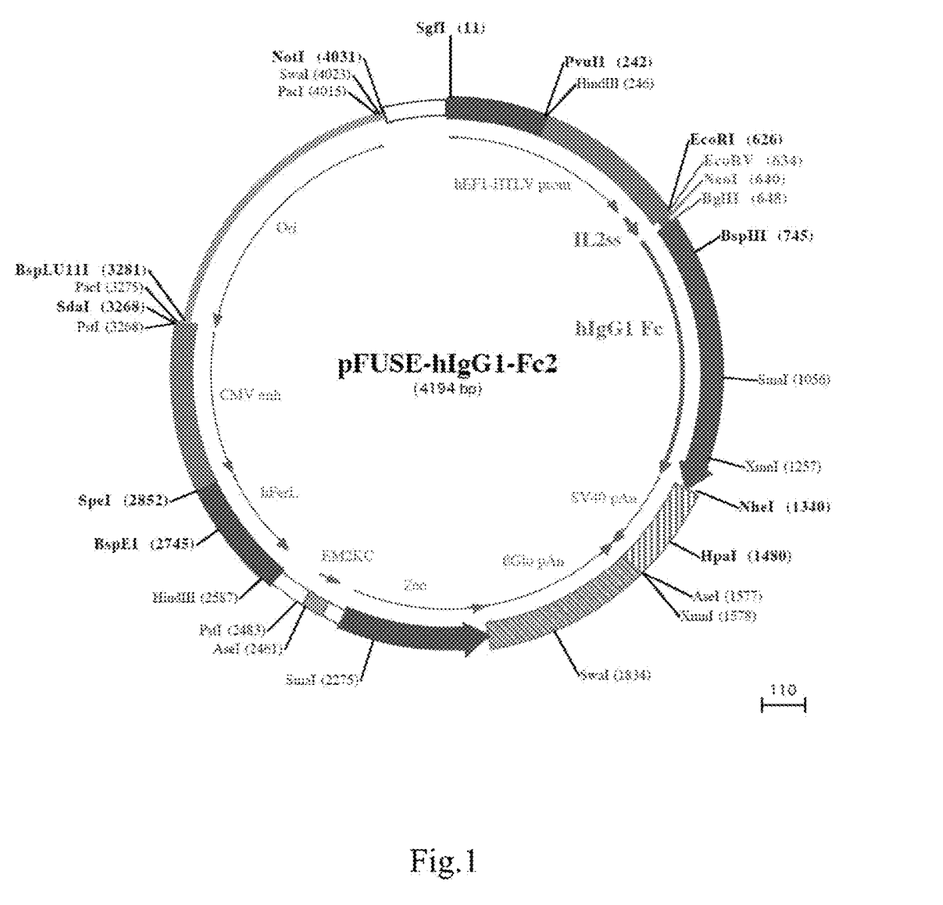
FIG. 1 shows the vector plasmid map used to construct collagen-RBD trimeric protein.

Based on the nucleotide sequence of the collagen-RBD fusion protein, GenScript Biotech Corporation (Nanjing, China) was entrusted to perform a gene synthesis. The synthesized gene fragment was linked to the pFUSE-hIgG1-Fc2 vector via the EcoR I and Nco I restriction sites (FIG. 1) to obtain the pFUSE-hIgG1-Fc2 vector containing the nucleotide sequence of the collagen-RBD fusion protein. The nucleotide sequence was verified to be correct after sequencing and the plasmid was transformed into DH5α competent cells. The specific steps were as follows.

1) A tube of DH5α competent cells was taken from −80° C. and placed on ice.
2) 1 μl of the constructed plasmid was added to the DH5α competent cells and placed on ice for 30 minutes.
3) The tube of the DH5α competent cells was heat shocked at 42° C. for 90 seconds, and quickly placed on ice.
4) After the tube was standed for 2 minutes, 600 μl of a LB medium without antibiotics was added, and the tube of cells was shaken in a shaker at 37° C. for 1 hour.
5) 100 μl of the culture was taken and plated on a LB plate containing bleomycin.

6) After colonies grown out, colonies in a single clone were picked up and added to 5 ml of a LB medium containing bleomycin. After 12 hours, 5 ml of the LB medium was transferred to 500 ml of a LB medium.

7) after 8 hours, the plasmid was extracted using Plasmid Extraction Maxi Kit (TIANGEN BIOTECH Co., LTD.).

Then the fusion protein collagen-RBD protein was expressed. The specific steps were as follows:

1) Well-grown EXPi293F cells were passaged to a density of $1\times10^6$/ml.

2) After 12 hours, the cells were transfected with the plasmid containing the nucleotide sequence encoding the collagen-RBD fusion protein according to the instructions of the EZ Trans cell transfection reagent (Life-iLab Biotech Co., Ltd.).

3) After the cells were cultured for additional 6 days, the cells were centrifuged at 2000 rpm and the cell supernatant was collected.

NI-NTA was used to purify the collagen-RBD fusion protein and the specific steps were as follows.

1) The collected cell supernatant was filtered through a 0.45 μm filter membrane.

2) 1 ml of NI-NTA (Qiagen) was added to the protein purification column.

3) 5 ml of ddH2O was added to remove alcohol from NI-NTA.

4) NI-NTA was equilibrated by adding 10 ml of a binding buffer (40 mM $NaH_2PO_3$, 500 mM NaCl, pH: 7.8).

5) The treated NI-NTA was added to the protein supernatant and incubated at 4° C. for 3 hours.

6) Protein impurities were then washed out using the binding buffer containing 5 mM imidazole in a total wash volume of 30 ml.

7) The protein of interest was eluted using the binding buffer containing 40 mM imidazole.

8) The eluted protein of interest was run on SDS-PAGE.

Figure 2:
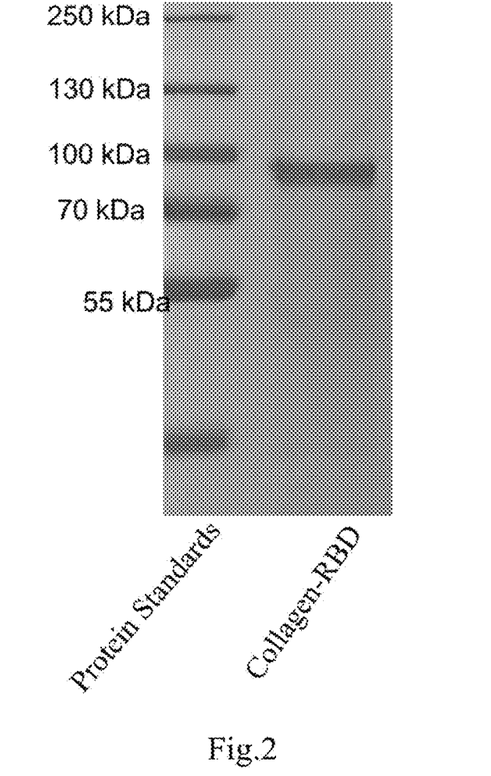
FIG. 2 is an SDS-PAGE image of the expressed collagen-RBD trimeric protein.

The results are shown in FIG. 2. The collagen-RBD fusion protein was successfully expressed, and a high-purity collagen-RBD fusion protein was obtained. After denaturation treatment, the molecular weight was approximately 80 kDa, consistent with the expected size.

Figure 3:
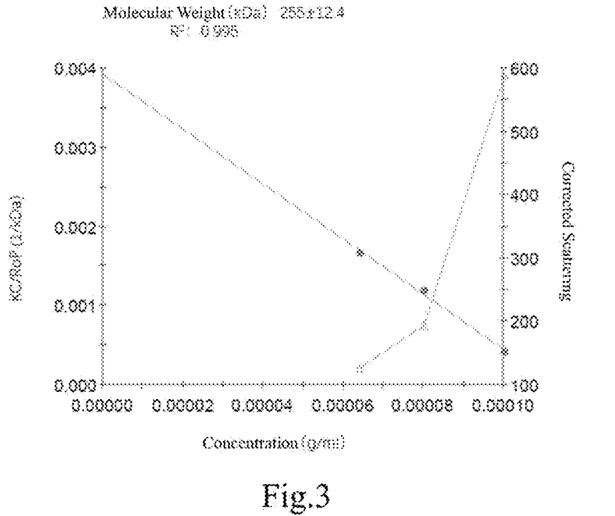
FIG. 3 shows the detection of the molecular weight of collagen-RBD trimeric protein using a particle size analyzer.

In order to verify whether the protein formed a trimer, a particle size analyzer was used to detect the molecular weight of the protein. The results showed that the predicted molecular weight of the collagen-RBD fusion protein was 255 kDa, which is approximately 3 times the molecular weight of the monomer (FIG. 3). Therefore, this collagen-RBD fusion protein was a trimeric protein.

Example 2: Comparison Between the Levels of RBD-Specific Binding Antibodies Produced by Mice Immunized with the Collagen-RBD Trimeric Protein and the RBD Monomer Protein Materials: Balb/c mice were purchased from Beijing Vital River Laboratory Animal Technology Co., Ltd. The aluminum adjuvant was purchased from Thermo Scientific. The RBD-His monomer protein was purchased from Kactus Biosystems (Shanghai) Co., Ltd. CF501 adjuvant has the following structure and was owned by the applicants' laboratory.

Figure 4:
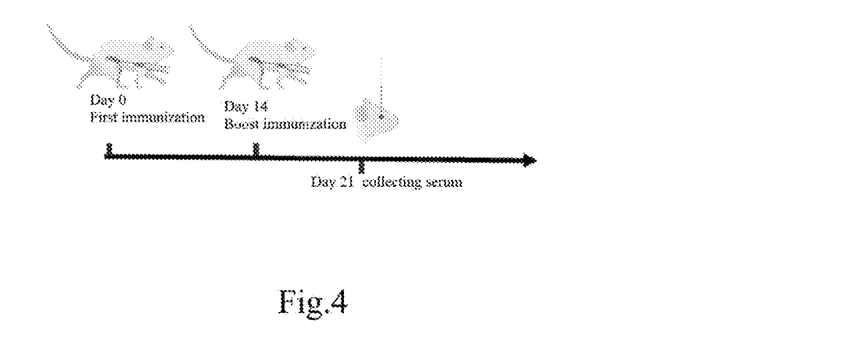
FIG. 4 shows the immunization schedule of mice.

Twenty-four 6-week old Balb/c mice were evenly divided into 4 groups, with 6 mice in each group. The first group of mice was injected intramuscularly with 5 μg of the collagen-RBD trimeric protein and 20 μg of CF501 adjuvant. The second group of mice was injected intramuscularly with 5 μg of the RBD monomer protein and 20 μg of CF501 adjuvant. The third group of mice was injected intramuscularly with 5 μg of the collagen-RBD trimeric protein and an equal volume of the aluminum adjuvant. The fourth group of mice was injected intramuscularly with 5 μg of the RBD monomeric protein and an equal volume of the aluminum adjuvant. The immunization schedule of mice is shown in FIG. 4. Mice were immunized twice on days 0 and 14, respectively, and the sera were collected from the mice on day 21. The sera of the mice were inactivated at 56° C. for 30 minutes.

The ELISA method was used to detect the titers of IgG antibodies specific to SARS-COV-2 RBD in the sera of mice. The specific steps were as follows.

1) 1 μg/ml of RBD-His monomer protein (Kactus Biosystems (Shanghai) Co., Ltd) was coated onto a ELISA plate and placed at 4° C. overnight for coating.

2) The ELISA plate was blocked, 200 μl of PBS containing 5% BSA was added to each well, and placed at 37° C. for 2 hours.

3) PBST was used to dilute the sera of the mice. The sera of the mice were diluted starting from 100-fold dilution and then in a 3-fold dilution.

4) The diluted sera of the mice were added to the ELISA plate and incubated at 37° C. for 45 minutes.

5) The ELISA plate was washed 5 times with PBST.

6) HRP-labeled rabbit anti-mouse IgG secondary antibody (Dako) was added and incubated at 37° C. for 45 minutes.

7) The ELISA plate was washed 5 times with PBST.

8) The TMB substrate was added to develop color for 15 minutes.

9) Color development was stopped by adding $H_2SO_4$.

10) A microplate reader was used to read out OD450 and the titers of antibodies in the sera were calculated.

Figure 5:
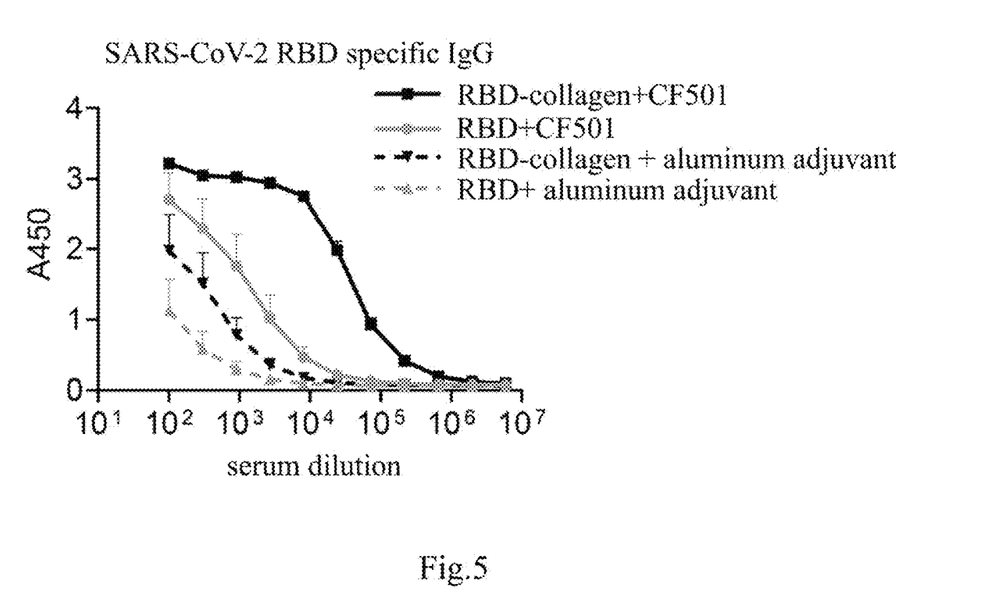
FIG. 5 shows the detection of levels of specific IgG binding antibodies to SARS-COV-2 RBD in the sera on day 21 after immunization of mice.
Figure 6:
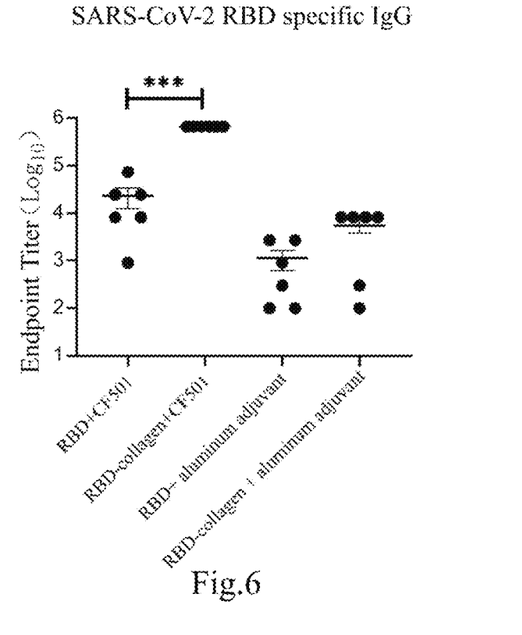
FIG. 6 shows the titer of specific IgG binding antibodies to SARS-COV-2 RBD in the sera on day 21 after immunization of mice.

The results are shown in FIG. 5, FIG. 6 and Table 1. After mice were immunized with CF501/collagen-RBD trimers, the average titer of IgG antibodies to SARS-COV-2 RBD in the sera reached 656,100, which was 28 times higher than the titer of RBD-specific IgG antibodies in the sera of mice immunized with CF501/RBD monomer. Furthermore, the titers of IgG antibodies in the sera of mice immunized with the aluminum adjuvant/collagen-RBD trimer was also nearly five times higher than those in the sera of mice immunized with the aluminum adjuvant/RBD monomer. These data indicate that the collagen-RBD trimeric protein as an immunogen can potently enhance the immunogenicity of RBD.

TABLE 1 titers of IgG antibodies specific to SARS-CoV-2 RBD in the sera on Day 21 after immunization of mice

| Mice Grouping | CF501/ Collagen-RBD | CF501/ RBD | Aluminum Adjuvant/ Collagen-RBD | Aluminum Adjuvant/ RBD |
|---|---|---|---|---|
| Titers of SARS-CoV-2 RBD-Specific IgG Mean ± S.E.) | 6561000 | 23100 ± 10686 | 5467 ± 1666 | 1133 ± 509 |

Example 3: The Collagen-RBD Trimeric Protein can Induce a Titer of Highly Potent Neutralizing Antibodies to a SARS-COV-2 Pseudovirus in Mice In order to compare the titers of neutralizing antibodies to SARS-COV-2 induced by the collagen-RBD trimer and the RBD monomer, the neutralizing effect on a SARS-COV-2 pseudovirus was tested in the sera after immunization of mice. SARS-COV-2 pseudovirus was packaged as follows.
1) Well-grown HEK-293T cells were passaged.
2) After 24 hours of incubation, HEK-293T cells were co-transfected with a backbone plasmid PNL-4-3 and a SARS-COV-2 envelope plasmid PcDNA3.1-SARS-COV-2-S (Liu, Z., Zhou, J., Xu, W. et al. A novel STING agonist-adjuvanted pan-sarbecovirus vaccine elicits potent and durable neutralizing antibody and T cell responses in mice, rabbits and NHPs. Cell Res 32, 269-287 (2022). https://doi.org/10.1038/s41422-022-00612-2) using Vigofect transfection reagent (Vigorous Biotechnology Beijing Co., Ltd.).
3) After 12 hours of incubation, the medium was replaced with a fresh DMEM medium containing 10% FBS.
4) After additional 48 hours of incubation, the cell supernatant was collected, and the SARS-COV-2 pseudovirus was obtained.

The experiment of neutralization on SARS-COV-2 pseudovirus was performed and described in particular as follows.
1) Well-grown Huh-7 cells was plated into a 96-well plate at 10,000 cells per well.
2) After 8 hours of incubation, the sera of the mice were diluted with DMEM.
3) The diluted sera of the mice were mixed with the SARS-COV-2 pseudovirus and incubated for 30 minutes.
4) The pseudovirus and the sera of the mice were added to Huh-7 cells.
5) After 12 hours of incubation, the medium was replaced with a fresh DMEM medium.
6) The luciferase value of each well was detected using a luciferase kit (Promega Corporation) after 48 hours.
7) The titers of neutralizing antibodies in sera were calculated.

Figure 7:
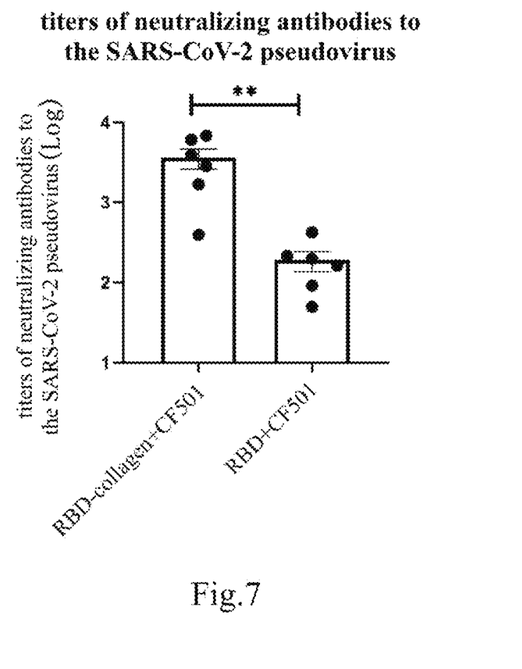
FIG. 7 shows the titers of neutralizing antibodies to SARS-COV-2 pseudovirus in the sera on day 21 after immunization of mice with CF501 adjuvanted collagen-RBD trimers or RBD monomers.
Figure 8:
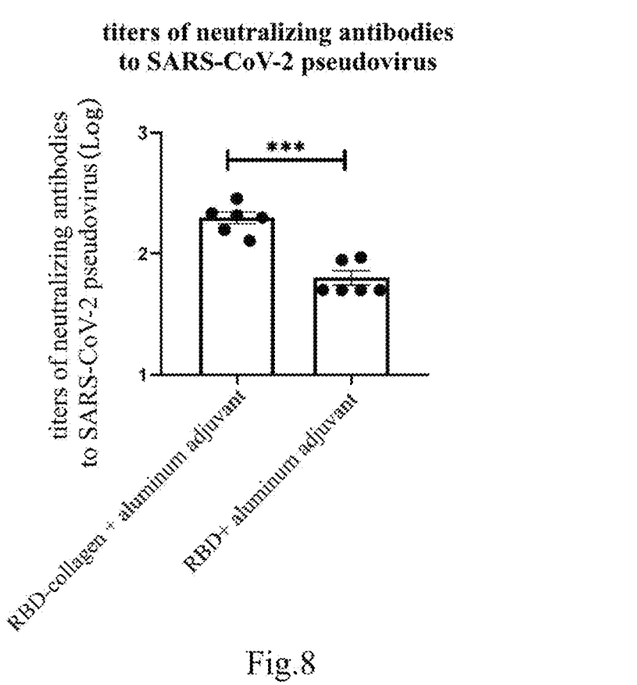
FIG. 8 shows the titers of neutralizing antibodies to SARS-COV-2 pseudovirus in the sera on day 21 after immunization of mice with aluminum-adjuvanted collagen-RBD trimers or RBD monomers.

The results are shown in FIG. 7, FIG. 8 and Table 2. The average titer of the neutralizing antibodies to SARS-COV-2 pseudovirus produced by the collagen-RBD trimeric protein with CF501 as adjuvant reached 3620, while the average titer of the neutralizing antibodies to SARS-COV-2 pseudovirus produced by the RBD monomer with CF501 as adjuvant was only 191. Similarly, the titer of the neutralizing antibodies in mice immunized with the aluminum adjuvanted collagen-RBD trimeric protein was also higher than that of mice immunized with the aluminum adjuvanted RBD monomer protein.

TABLE 2

Titers of neutralizing antibodies to SARS-CoV-2 pseudovirus in the sera on Day 21 after immunization of mice

| Mice Grouping | CF501/ Collagen-RBD | CF501/ RBD | Aluminum Adjuvant/ Collagen-RBD | Aluminum Adjuvant/ RBD |
|---|---|---|---|---|
| Titers of neutralizing Antibodies to SARS-CoV-2 pseudovirus (Mean ± S.E.) | 3620 ± 1017 | 191.3 ± 54 | 198.6 ± 22 | 63.66 ± 9 |

Example 4: Comparison of the Levels of Antibodies Specifically Binding to HA1 Produced after Immunization of Mice with a Collagen-H1N1 HA1 Trimeric Protein and an H1N1 HA1 Monomer Protein Construction and Expression of a Recombinant Type III Collagen-H1N1 HA1 Trimeric Protein Based on the nucleotide sequence of the collagen-H1N1 HA1 fusion protein, GenScript Biotech Corporation (Nanjing, China) was entrusted to perform gene synthesis. The synthesized gene fragment was linked to the pFUSE-hIgG1-Fc2 vector via the EcoR I and Nco I restriction sites to obtain the pFUSE-hIgG1-Fc2 vector containing the nucleotide sequence of the collagen-H1N1 HA1 fusion protein. The collagen-HA1 fusion protein was expressed according to the protein expression procedure in Example 1.

Twenty-four 6-week old Balb/c mice were evenly divided into 4 groups, with 6 mice in each group. The first group of mice was injected intramuscularly with 5 µg of the collagen-H1N1 HA1 trimeric protein and 20 µg of CF501 adjuvant. The second group of mice was injected intramuscularly with 5 µg of the H1N1 HA1 monomer protein and 20 µg of CF501 adjuvant. The third group of mice was injected intramuscularly with 5 µg of the collagen-H1N1 HA1 trimeric protein and an equal volume of aluminum adjuvant. The fourth group of mice was injected intramuscularly with 5 µg of the H1N1 HA1 monomeric protein and an equal volume of aluminum adjuvant. The immunization schedule of mice is shown in FIG. 4. Mice were immunized twice on days 0 and 14, respectively, and the sera were collected from the mice on day 21. The sera of the mice were inactivated at 56° C. for 30 minutes.

The ELISA method was used to detect the titers of the IgG antibodies specific to the H1N1 HA1 in the sera of the mice. The specific steps were as follows:
1) 1 µg/ml of the H1N1 HA1-His monomeric protein was coated onto an ELISA plate and placed at 4° C. overnight for coating.

2) The ELISA plate was blocked, 200 μl of PBS containing 5% BSA was added to each well, and placed at 37° C. for 2 hours.
3) PBST was used to dilute the sera of the mice. The sera of the mice were diluted starting from 100-fold dilution and then in 3-fold dilution.
4) The diluted sera of mice were added to the ELISA plate and incubated at 37° C. for 45 minutes.
5) The ELISA plate was washed 5 times with PBST.
6) HRP-labeled rabbit anti-mouse IgG secondary antibody (Dako) was added and incubated at 37° C. for 45 minutes.
7) The ELISA plate was washed 5 times with PBST.
8) The TMB substrate was added to develop color for 15 minutes.
9) Color development was stopped by adding $H_2SO_4$.
10) A microplate reader was used to read out OD450 and the titers of the antibodies in the sera were calculated.

Figure 9:
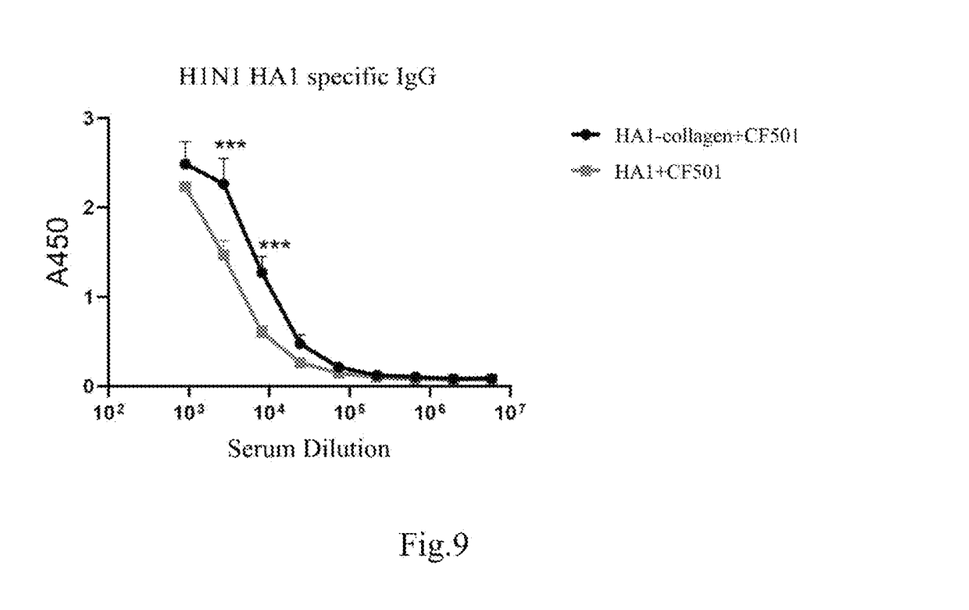
FIG. 9 shows the detection of levels of IgG binding antibodies specific to H1N1 HA1 in the sera on day 17 after immunization of mice with influenza HA1-collagen/CF501 and HA1/CF501.
Figure 10:
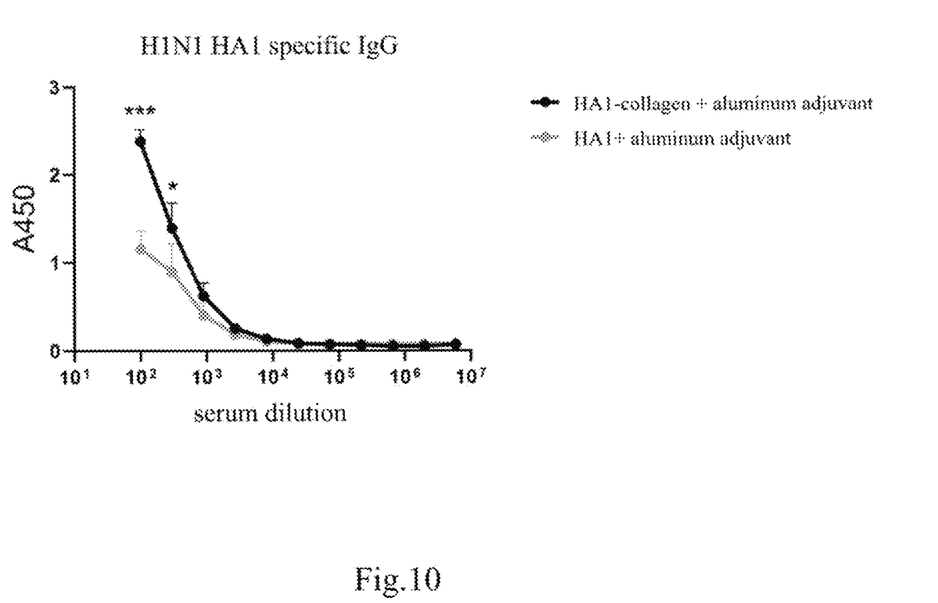
FIG. 10 shows the detection of levels of IgG binding antibodies specific to H1N1 HA1 in the sera on day 17 after immunization of mice with influenza HA1-collagen/aluminum adjuvant and HA1/aluminum adjuvant.

The results are shown in FIGS. 9 and 10. Whether using CF501 adjuvant or aluminum adjuvant, the H1N1 HA1 protein with the tagged collagen can produce higher levels of IgG antibodies to the HA1 protein than the H1N1 HA1 protein alone. Therefore, the collagen trimerization tag or region can significantly improve the immunogenicity of antigens, irrespective of antigens of the novel coronavirus or antigens of influenza viruses.

```
Sequences
Repeating unit in the trimerization region:
                                                      (SEQ ID NO. 1)
GERGAPGFRGPAGPNGIPGEKGPAGERGAP.

The region at the C-terminus of the trimerization region:
                                                      (SEQ ID NO. 2)
GAPGPCCGG.

Exemplary trimerization region:
                                                      (SEQ ID NO. 3)
GERGAPGFRGPAGPNGIPGEKGPAGERGAPGERGAPGFRGPAGPNGIPGEKGPAGERG

APGERGAPGFRGPAGPNGIPGEKGPAGERGAPGERGAPGFRGPAGPNGIPGEKGPAGE

RGAPGERGAPGFRGPAGPNGIPGEKGPAGERGAPGERGAPGFRGPAGPNGIPGEKGPA

GERGAPGERGAPGFRGPAGPNGIPGEKGPAGERGAPGERGAPGFRGPAGPNGIPGEKG

PAGERGAPGERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRGPAGPNGIP

GEKGPAGERGAPGERGAPGFRGPAGPNGIPGEKGPAGERGAPGERGAPGFRGPAGPN

GIPGEKGPAGERGAPGERGAPGFRGPAGPNGIPGEKGPAGERGAPGERGAPGFRGPAG

PNGIPGEKGPAGERGAPGAPGPCCGG.

Exemplary immunogenic region (the amino acid sequence of the
SARS-CoV-2 RBD protein):
                                                      (SEQ ID NO. 4)
RVQPTESIVRFPNITNLCPFGEVENATRFASVYAWNRKRISNCVADYSVLYNSASFSTF

KCYGVSPTKLNDLCFTNVYADSFVIRGDEVRQIAPGQTGKIADYNYKLPDDFTGCVIA

WNSNNLDSKVGGNYNYRYRLFRKSNLKPFERDISTEIYQAGSKPCNGVEGENCYFPLQ

SYGFQPTNGVGYQPYRVVVLSFELLHAPATVCGPKKSTN.

Exemplary fusion protein (without His tag):
                      (SEQ ID NO. 5, trimerization
                      region underlined, immunogenicity region in bold)
GERGAPGFRGPAGPNGIPGEKGPAGERGAPGERGAPGFRGPAGPNGIPGEKGPAGERG

APGERGAPGFRGPAGPNGIPGEKGPAGERGAPGERGAPGFRGPAGPNGIPGEKGPAGE

RGAPGERGAPGFRGPAGPNGIPGEKGPAGERGAPGERGAPGFRGPAGPNGIPGEKGPA

GERGAPGERGAPGFRGPAGPNGIPGEKGPAGERGAPGERGAPGFRGPAGPNGIPGEKG

PAGERGAPGERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRGPAGPNGIP

GEKGPAGERGAPGERGAPGFRGPAGPNGIPGEKGPAGERGAPGERGAPGFRGPAGPN

GIPGEKGPAGERGAPGERGAPGFRGPAGPNGIPGEKGPAGERGAPGERGAPGFRGPAG

PNGIPGEKGPAGERGAPGAPGPCCGGGGGGGSGGGGSGGGGSGGGGSRVQPTESIVRF

PNITNLCPFGEVENATRFASVYAWNRKRISNCVADYSVLYNSASFSTFKCYGVSPT

KLNDLCFTNVYADSFVIRGDEVRQIAPGQTGKIADYNYKLPDDFTGCVIAWNSNN
```

-continued

LDSKVGGNYNYRYRLFRKSNLKPFERDISTEIYQAGSKPCNGVEGENCYFPLQSY

GFQPTNGVGYQPYRVVVLSFELLHAPATVCGPKKSTN.

Exemplary fusion protein (with His tag):
(SEQ ID NO. 6, His tag in bold)
GERGAPGFRGPAGPNGIPGEKGPAGERGAPGERGAPGFRGPAGPNGIPGEKGPAGERG

APGERGAPGFRGPAGPNGIPGEKGPAGERGAPGERGAPGFRGPAGPNGIPGEKGPAGE

RGAPGERGAPGFRGPAGPNGIPGEKGPAGERGAPGERGAPGFRGPAGPNGIPGEKGPA

GERGAPGERGAPGFRGPAGPNGIPGEKGPAGERGAPGERGAPGFRGPAGPNGIPGEKG

PAGERGAPGERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRGPAGPNGIP

GEKGPAGERGAPGERGAPGFRGPAGPNGIPGEKGPAGERGAPGERGAPGFRGPAGPN

GIPGEKGPAGERGAPGERGAPGFRGPAGPNGIPGEKGPAGERGAPGERGAPGFRGPAG

PNGIPGEKGPAGERGAPGAPGPCCGGGGGSGGGGSGGGGSGGGGSRVQPTESIVRFP

NITNLCPFGEVENATRFASVYAWNRKRISNCVADYSVLYNSASFSTFKCYGVSPTKLN

DLCFTNVYADSFVIRGDEVRQIAPGQTGKIADYNYKLPDDFTGCVIAWNSNNLDSKVG

GNYNYRYRLFRKSNLKPFERDISTEIYQAGSKPCNGVEGENCYFPLQSYGFQPTNGVG

YQPYRVVVLSFELLHAPATVCGPKKSTNHHHHHHHH.

Exemplary fusion protein coding sequences:
(SEQ ID NO. 7)
GGAGAACGTGGAGCCCCGGATTCAGAGGACCAGCCGGCCCCAACGGAATCCCTG

GTGAGAAGGGCCCTGCCGGCGAAAGGGGCGCCCCGGGCGAGAGAGGAGCCCCTG

GCTTCCGGGGCCCGGCCGGGCCTAATGGCATCCCTGGCGAGAAGGGCCCTGCTGG

AGAACGGGGCGCCCCCGGCGAGCGCGGAGCTCCCGGCTTCCGGGGCCCAGCCGGG

CCTAACGGCATCCCTGGCGAGAAGGGCCCTGCCGGCGAGAGGGGCGCTCCTGGGG

AGAGAGGCGCCCCTGGCTTCAGAGGACCCGCCGGTCCTAATGGAATCCCCGGCGA

GAAGGGCCCTGCCGGCGAAAGAGGCGCCCCTGGAGAGAGAGGCGCTCCTGGATTT

AGAGGTCCAGCCGGTCCCAACGGAATCCCTGGAGAGAAGGGGCCCGCTGGCGAA

AGAGGAGCCCCTGGCGAAAGAGGCGCCCCCGGATTTAGAGGACCTGCAGGCCCTA

ATGGAATCCCTGGCGAGAAGGGCCCTGCCGGAGAACGGGGCGCCCCTGGCGAGA

GAGGTGCCCCTGGCTTTAGAGGCCCCGCTGGCCCCAACGGCATCCCTGGGGAGAA

AGGCCCGGCCGGCGAACGGGGAGCCCCGGGCGAGAGGGGCGCCCCAGGATTCCG

GGGCCCTGCTGGCCCCAACGGCATTCCTGGCGAAAAAGGCCCTGCCGGGGAGCGG

GGCGCCCCTGGCGAAAGAGGCGCTCCTGGTTTCCGGGGCCCTGCTGGGCCTAACG

GCATCCCCGGCGAAAAGGGCCCAGCCGGGGAGAGAGGAGCCCCTGGCGAGCGGG

GAGCTCCTGGCTTCAGAGGCCCTGCCGGCCCTAACGGCATCCCCGGCGAAAAAGG

CCCCGCCGGTGAAAGAGGGGCGCCCGGTGAAAGAGGCGCCCCTGGCTTCCGGGGC

CCTGCCGGCCCAAATGGTATCCCTGGAGAAAAGGGCCCTGCAGGAGAGCGTGGCG

CCCCTGGCGAACGCGGCGCCCCTGGCTTTAGAGGCCCAGCAGGCCCTAACGGCAT

CCCTGGCGAGAAAGGACCCGCTGGTGAAAGAGGCGCCCCAGGCGAGAGAGGGGC

TCCTGGCTTCAGAGGCCCAGCCGGCCCAAACGGCATCCCTGGCGAGAAGGGCCCC

GCCGGCGAACGGGGCGCCCCGGGCGAGAGAGGAGCCCCCGGTTTCCGGGGTCCCG

CCGGCCCTAATGGCATCCCCGGCGAGAAAGGACCTGCCGGCGAGCGGGGCGCTCC

-continued

```
TGGAGAGCGGGGCGCCCCTGGCTTCCGGGGCCCTGCTGGCCCTAACGGAATCCCT

GGCGAAAAAGGCCCTGCCGGCGAGAGAGGCGCCCCCGGCGAGAGAGGGGCCCCA

GGCTTCCGGGGACCTGCCGGCCCTAACGGCATCCCTGGCGAGAAGGGCCCTGCTG

GCGAAAGAGGCGCCCCCGGAGCGCCTGGCCCCTGTTGCGGCGGAGGAGGAGGTG

GATCTGGCGGCGGAGGCAGCGGAGGCGGCGGCTCTGGGGGCGGCGGCTCCAGAG

TGCAGCCTACAGAGAGCATCGTGCGGTTCCCCAACATCACCAACCTGTGTCCTTTC

GGTGAGGTGTTCAACGCTACCAGATTCGCCAGCGTGTACGCCTGGAATAGAAAGA

GAATCAGCAATTGCGTGGCCGACTACAGCGTGCTGTACAACAGCGCCTCTTTCAGC

ACCTTCAAGTGCTATGGCGTGTCCCCTACCAAGCTGAACGACCTGTGCTTCACCAA

CGTGTACGCCGACAGCTTCGTGATCAGAGGCGATGAGGTGAGACAGATCGCCCCT

GGCCAGACCGGCAAGATCGCCGATTACAACTACAAGCTGCCTGACGACTTCACCG

GTTGTGTGATCGCCTGGAACAGCAACAACCTGGACAGCAAGGTGGGCGGAAATTA

CAACTACAGATACAGACTGTTCAGAAAGTCCAACCTCAAGCCCTTCGAGAGAGAT

ATCTCTACAGAAATCTACCAGGCCGGATCTAAGCCTTGCAACGGCGTGGAAGGCT

TTAACTGCTACTTCCCTCTGCAGAGCTACGGCTTTCAGCCCACCAACGGCGTTGGT

TATCAACCTTACAGAGTCGTGGTCCTGAGCTTTGAGCTGCTGCACGCCCCTGCTAC

AGTGTGCGGCCCCAAGAAGAGCACAAACCACCACCACCACCACCACCATTGA.

Exemplary linker:
                                                   (SEQ ID NO. 8)
GGGGSGGGGGGGSGGGGS.

Collagen-H1N1 HA1 fusion protein (with His tag):
                                                   (SEQ ID NO. 9)
GERGAPGFRGPAGPNGIPGEKGPAGERGAPGERGAPGFRGPAGPNGIPGEKGPAGERG

APGERGAPGFRGPAGPNGIPGEKGPAGERGAPGERGAPGFRGPAGPNGIPGEKGPAGE

RGAPGERGAPGFRGPAGPNGIPGEKGPAGERGAPGERGAPGFRGPAGPNGIPGEKGPA

GERGAPGERGAPGFRGPAGPNGIPGEKGPAGERGAPGERGAPGFRGPAGPNGIPGEKG

PAGERGAPGERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRGPAGPNGIP

GEKGPAGERGAPGERGAPGFRGPAGPNGIPGEKGPAGERGAPGERGAPGFRGPAGPN

GIPGEKGPAGERGAPGERGAPGFRGPAGPNGIPGEKGPAGERGAPGERGAPGFRGPAG

PNGIPGEKGPAGERGAPGAPGPCCGGGGGGSGGGGSGGGGSGGGGSDTICIGYHANN

STDTVDTIFEKNVAVTHSVNLLEDRHNGKLCKLKGIAPLQLGKCNIIGWLLGNPECDS

LLPARSWSYIVETPNSENGACYPGDFIDYEELREQLSSVSSLERFEIFPKESSWPNHTFN

GVTASCSHRGKSSFYRNLLWLTKKGDSYPKLTNSYVNNKGKEVLVLWGVHHPSSSDE

QQSLYSNGNAYVSVASSNYNRRFTPEIAARPKVKDQHGRMNYYWTLLEPGDTIIFEAT

GNLIAPWYAFALSRGFESGIITSNASMHECNTKCQTPQGSINSNLPFQNIHPVTIGECPK

YVRSTKLRMVTGLRNIPSIQYRHHHHHHHH.

Influenza virus H1N1 (A/WSN/1933) HA1 protein amino acid sequence:
                                                   (SEQ ID NO. 10)
DTICIGYHANNSTDTVDTIFEKNVAVTHSVNLLEDRHNGKLCKLKGIAPLQLGKCNIIG

WLLGNPECDSLLPARSWSYIVETPNSENGACYPGDFIDYEELREQLSSVSSLERFEIFPK

ESSWPNHTFNGVTASCSHRGKSSFYRNLLWLTKKGDSYPKLTNSYVNNKGKEVLVL

WGVHHPSSSDEQQSLYSNGNAYVSVASSNYNRRFTPEIAARPKVKDQHGRMNYYWT
```

-continued

LLEPGDTIIFEATGNLIAPWYAFALSRGFESGIITSNASMHECNTKCQTPQGSINSNLPFQ

NIHPVTIGECPKYVRSTKLRMVTGLRNIPSIQYR.

The invention claimed is:

1. A fusion protein comprising a trimerization region and an immunogenicity region linked by a linker, wherein the trimerization region comprises one or more repeating units as set forth in SEQ ID NO. 1; the immunogenicity region is an immunogenic protein of a pathogen, for example selected from the group consisting of a coronavirus RBD region, a HIV membrane protein or an influenza virus hemagglutinin protein and their immunogenic fragments, preferably the influenza virus hemagglutinin protein is H1N1 HA1 protein.

2. The fusion protein according to claim 1, wherein the trimerization region comprises 10-20, such as 11, 12, 13, 14, 15, 16, 17, 18 or 19 repeating units as set forth in SEQ ID NO. 1, and optionally comprises one or more stabilization regions as set forth in SEQ ID NO. 2 at the C-terminus, and the repeating unit is directly linked to the stabilization region or separated from the stabilization region by one or more amino acid residues.

3. The fusion protein according to claim 1 or 2, wherein the trimerization region comprises the amino acid sequence as set forth in SEQ ID NO. 3, and/or the immunogenic region comprises the amino acid sequence as set forth in SEQ ID NO. 4 or SEQ ID NO. 10, and/or the linker is (GGGS)n or (GGGGS)n or (G)n, preferably n is an integer from 1 to 10, such as 2, 3, 4, 5, 6, 7, 8 or 9.

4. The fusion protein according to claim 1, wherein the trimerization region and the immunogenicity region are respectively located at the N-terminus and C-terminus of the fusion protein; preferably, the fusion protein comprises the amino acid sequence as set forth in SEQ ID NO. 5 or 9.

5. A nucleic acid comprising nucleotides encoding the fusion protein according to claim 1, wherein optionally, the nucleic acid further comprises nucleotides encoding a purification tag, such as a His tag, a GST tag, an MBP tag, a SUMO tag, or a NusA tag; optionally, the nucleic acid further comprises a nucleotide encoding a leader sequence; preferably, the nucleic acid comprises the sequence as set forth in SEQ ID NO. 7.

6. A vector comprising the nucleic acid according to claim 5, optionally comprising an expression control element operably linked to the nucleic acid, such as a promoter, a terminator and/or an enhancer.

7. A host cell comprising a nucleic acid according to claim 5; wherein preferably the host cell is a eukaryotic cell or a prokaryotic cell; wherein preferably the eukaryotic cell is a yeast cell, an animal cell and/or an insect cell, and/or the prokaryotic cell is an *E. coli* cell.

8. A trimeric fusion protein comprising the fusion protein according to claim 1.

9. A method for producing the fusion protein according to claim 1, comprising:

(1) cultivating a host cell under an appropriate culture condition;

(2) harvesting the host cells and/or culture medium containing the fusion protein or trimeric fusion protein; and (3) purifying the fusion protein or trimeric fusion protein.

10. A composition comprising the fusion protein according to claim 1.

11. The composition according to claim 10, wherein the composition is a pharmaceutical composition, in particular a vaccine, and further comprises a pharmaceutically acceptable carrier, excipient, diluent and/or adjuvant, such as an aluminum adjuvant, a saponin adjuvant, a lipid A, a monophosphoryl lipid A, a trehalose dimycolate, an oil emulsion adjuvant, a polysaccharide adjuvant, a Toll-like receptor activator and/or a STING agonist;

preferably, the adjuvant is

12. Use of the fusion protein according to claim 1 in the manufacture of a medicament for the treatment or prevention of a condition or a disease mediated by a pathogen, preferably the pathogen is a virus, bacterium, fungus and/or parasite, preferably, the virus is selected from the group consisting of a coronavirus, HIV, and an influenza virus, preferably, the influenza virus is influenza A virus or influenza B virus, preferably, the coronavirus is SARS-COV-2.

13. Use of the trimeric fusion protein according to claim 8 in the manufacture of a medicament for the treatment or prevention of conditions or diseases mediated by a pathogen, preferably the pathogen is a virus, bacterium, fungi and/or parasite, preferably, the virus is selected from coronavirus, HIV, and influenza virus, preferably, the influenza virus is influenza A virus or influenza B virus, preferably, the coronavirus is SARS-COV-2.

* * * * *

```
                            SEQUENCE LISTING

Sequence total quantity: 10
SEQ ID NO: 1            moltype = AA   length = 30
FEATURE                 Location/Qualifiers
source                  1..30
                        mol_type = protein
                        organism = synthetic construct
SEQUENCE: 1
GERGAPGFRG PAGPNGIPGE KGPAGERGAP                                      30

SEQ ID NO: 2            moltype = AA   length = 9
FEATURE                 Location/Qualifiers
REGION                  1..9
                        note = C
source                  1..9
                        mol_type = protein
                        organism = synthetic construct
SEQUENCE: 2
GAPGPCCGG                                                              9

SEQ ID NO: 3            moltype = AA   length = 489
FEATURE                 Location/Qualifiers
REGION                  1..489
                        note = tri region
source                  1..489
                        mol_type = protein
                        organism = synthetic construct
SEQUENCE: 3
GERGAPGFRG PAGPNGIPGE KGPAGERGAP GERGAPGFRG PAGPNGIPGE KGPAGERGAP      60
GERGAPGFRG PAGPNGIPGE KGPAGERGAP GERGAPGFRG PAGPNGIPGE KGPAGERGAP     120
GERGAPGFRG PAGPNGIPGE KGPAGERGAP GERGAPGFRG PAGPNGIPGE KGPAGERGAP     180
GERGAPGFRG PAGPNGIPGE KGPAGERGAP GERGAPGFRG PAGPNGIPGE KGPAGERGAP     240
GERGAPGFRG PAGPNGIPGE KGPAGERGAP GERGAPGFRG PAGPNGIPGE KGPAGERGAP     300
GERGAPGFRG PAGPNGIPGE KGPAGERGAP GERGAPGFRG PAGPNGIPGE KGPAGERGAP     360
GERGAPGFRG PAGPNGIPGE KGPAGERGAP GERGAPGFRG PAGPNGIPGE KGPAGERGAP     420
GERGAPGFRG PAGPNGIPGE KGPAGERGAP GERGAPGFRG PAGPNGIPGE KGPAGERGAP     480
GAPGPCCGG                                                            489

SEQ ID NO: 4            moltype = AA   length = 214
FEATURE                 Location/Qualifiers
REGION                  1..214
                        note = SARS-CoV-2 RBD protein
source                  1..214
                        mol_type = protein
                        organism = synthetic construct
SEQUENCE: 4
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYRYRLFRK SNLKPFERDI STEIYQAGSK PCNGVEGFNC YFPLQSYGFQ  180
PTNGVGYQPY RVVVLSFELL HAPATVCGPK KSTN                               214

SEQ ID NO: 5            moltype = AA  length = 723
FEATURE                 Location/Qualifiers
REGION                  1..723
                        note = fusion protein without his tag
source                  1..723
                        mol_type = protein
                        organism = synthetic construct
SEQUENCE: 5
GERGAPGFRG PAGPNGIPGE KGPAGERGAP GERGAPGFRG PAGPNGIPGE KGPAGERGAP  60
GERGAPGFRG PAGPNGIPGE KGPAGERGAP GERGAPGFRG PAGPNGIPGE KGPAGERGAP  120
GERGAPGFRG PAGPNGIPGE KGPAGERGAP GERGAPGFRG PAGPNGIPGE KGPAGERGAP  180
GERGAPGFRG PAGPNGIPGE KGPAGERGAP GERGAPGFRG PAGPNGIPGE KGPAGERGAP  240
GERGAPGFRG PAGPNGIPGE KGPAGERGAP GERGAPGFRG PAGPNGIPGE KGPAGERGAP  300
GERGAPGFRG PAGPNGIPGE KGPAGERGAP GERGAPGFRG PAGPNGIPGE KGPAGERGAP  360
GERGAPGFRG PAGPNGIPGE KGPAGERGAP GERGAPGFRG PAGPNGIPGE KGPAGERGAP  420
GERGAPGFRG PAGPNGIPGE KGPAGERGAP GERGAPGFRG PAGPNGIPGE KGPAGERGAP  480
GAPGPCCGGG GGGSGGGGSG GGGSGGGGSR VQPTESIVRF PNITNLCPFG EVFNATRFAS  540
VYAWNRKRIS NCVADYSVLY NSASFSTFKC YGVSPTKLND LCFTNVYADS FVIRGDEVRQ  600
IAPGQTGKIA DYNYKLPDDF TGCVIAWNSN NLDSKVGGNY NYRYRLFRKS NLKPFERDIS  660
```

```
TEIYQAGSKP CNGVEGFNCY FPLQSYGFQP TNGVGYQPYR VVVLSFELLH APATVCGPKK    720
STN                                                                  723

SEQ ID NO: 6            moltype = AA  length = 731
FEATURE                 Location/Qualifiers
REGION                  1..731
                        note = His
source                  1..731
                        mol_type = protein
                        organism = synthetic construct
SEQUENCE: 6
GERGAPGFRG PAGPNGIPGE KGPAGERGAP GERGAPGFRG PAGPNGIPGE KGPAGERGAP     60
GERGAPGFRG PAGPNGIPGE KGPAGERGAP GERGAPGFRG PAGPNGIPGE KGPAGERGAP    120
GERGAPGFRG PAGPNGIPGE KGPAGERGAP GERGAPGFRG PAGPNGIPGE KGPAGERGAP    180
GERGAPGFRG PAGPNGIPGE KGPAGERGAP GERGAPGFRG PAGPNGIPGE KGPAGERGAP    240
GERGAPGFRG PAGPNGIPGE KGPAGERGAP GERGAPGFRG PAGPNGIPGE KGPAGERGAP    300
GERGAPGFRG PAGPNGIPGE KGPAGERGAP GERGAPGFRG PAGPNGIPGE KGPAGERGAP    360
GERGAPGFRG PAGPNGIPGE KGPAGERGAP GERGAPGFRG PAGPNGIPGE KGPAGERGAP    420
GERGAPGFRG PAGPNGIPGE KGPAGERGAP GERGAPGFRG PAGPNGIPGE KGPAGERGAP    480
GAPGPCCGGG GGGSGGGGSG GGGSGGGGSR VQPTESIVRF PNITNLCPFG EVFNATRFAS    540
VYAWNRKRIS NCVADYSVLY NSASFSTFKC YGVSPTKLND LCFTNVYADS FVIRGDEVRQ    600
IAPGQTGKIA DYNYKLPDDF TGCVIAWNSN NLDSKVGGNY NYRYRLFRKS NLKPFERDIS    660
TEIYQAGSKP CNGVEGFNCY FPLQSYGFQP TNGVGYQPYR VVVLSFELLH APATVCGPKK    720
STNHHHHHHH H                                                        731

SEQ ID NO: 7            moltype = DNA  length = 2196
FEATURE                 Location/Qualifiers
misc_feature            1..2196
                        note = nucleic acid encoding the fusion protein
source                  1..2196
                        mol_type = other DNA
                        organism = synthetic construct
SEQUENCE: 7
ggagaacgtg gagccccggg attcagagga ccagccggcc caacggaat ccctggtgag      60
aagggccctg ccggcgaaag gggcgccccg gcgagagag gagcccctgg cttcaggggc    120
ccggccgggc taatggcat ccctggcgag aagggccctg ctggagaacg gggcgccccc    180
ggcgagcgcg gagctcccgg cttccggggc ccagccgggc taacggcat ccctggcgag    240
aagggccctg ccggcgagag gggcgctcct ggggagagag gcgcccctgg cttcagagga    300
cccgccggtc ctaatggaat ccccggcgag aagggccctg ccggcgaaag aggcgccccc    360
ggagagagag gcgctcctgg attagaggt ccagccggtc caacggaat ccctgggag      420
aaggggcccg ctggcgaaag aggagcccct ggcgaaagag gcgccccgg atttagagga    480
cctgcaggcc taatggaat ccctggcgag aagggccctg ccggagaacg gggcgcccct    540
ggcgagagag gtgcccctgg ctttagaggc ccgctgggc caacggcat ccctggggag    600
aaaggcccgg ccggcgaacg gggagccccg gcgagagg gcgccccagg attccgggc      660
cctgctggcc caacggcat tcctggcgaa aaggggcctg ccggggagcg gggcgccct    720
ggcgaaagag gcgctcctgg tttccgggc cctgctggg ctaacggcat ccccggcgaa    780
aagggcccag ccggggagag aggagcccct ggcgagcggg gagctcctgg cttcagggag    840
cctgccggcc ctaacggcat ccccggcgaa aaggccccg ccggtgaaag aggggcgccc    900
ggtgaaagag gcgccccctgg cttccggggc cctgccggcc caaatggtat ccctggaaaa    960
aagggccctg caggagagcg tggcgcccct ggcgaacgcg gcgcccctgg ctttagaggc   1020
ccagcaggcc ctaacggcat ccctggcgag aaaggaccccg ctggtgaaag aggcgcccca   1080
ggcgagaaga ggactcctgg cttcagaggc cagccggtc caaacggcat ccctggcgac   1140
aagggccccg ccggcgaacg gggagccccg gcgagagag gagccccggg tttccgggt    1200
cccgccggcc ctaatggcat ccctggcgag aagggaccctg ccggcgagcg gggcgctcct   1260
ggagagcggg gcgcccctgg cttccggggc cctgctggcc caacggaat ccctggcgaa   1320
aaggccctg ccggcgagag aggcgcccccc ggcgagagag gggcccccagg cttccgggga    1380
cctgccggcc taacggcat ccctggcgag aagggcccctg ctggcgaaag aggcgccccc   1440
ggagcgcctg gccccctgttg cggcggagga ggagggtggat ctggcggcg aggcagcgga   1500
ggcggcggct ctggggggcg cggtccagga gtgcagccta cagagagcat cgtgcggttc   1560
cccaacatca ccaacctgtg tcctttcggt gaggtgttca cgctaccag attcgccagc   1620
gtgtacgcct ggaatagaaa gagaatcagc aattgcgtgg ccgactacag cgtgctgtac   1680
aacagccct ctttcagcac cttcaagtgc tatggcgtgt ccctaccaa gctgaacgac   1740
ctgtgcttca ccaacgtgta cgccgacagc ttcgtgatca gaggcgatga ggtgagacag   1800
atcgcccctg ccagaccggg caagatcgcc gattacaact acaagctgcc tgacgacttc   1860
accggttgtg tgatcgcctg gaacagcaac aacctggaca gcaaggtggg cggaaattac   1920
aactacagat acagactgtt cagaaagtcc aacctcaagc ccttcgagag agatatctct   1980
acagaaatct accaggccgg atctaagcct tgcaacggcg tggaaggctt taactgctac   2040
ttccctctgc agagctacgg ctttcagccc accaacggcg ttggtatca accttacaga   2100
gtcgtggtcc tgagctttga gctgctgcac gcccctgcta cagtgtgcgg ccccaagaag   2160
agcacaaacc accaccacca ccaccaccac cattga                             2196

SEQ ID NO: 8            moltype = AA  length = 20
FEATURE                 Location/Qualifiers
REGION                  1..20
                        note = linker
source                  1..20
                        mol_type = protein
                        organism = synthetic construct
```

```
SEQUENCE: 8
GGGGSGGGGS GGGGSGGGGS                                                       20

SEQ ID NO: 9           moltype = AA  length = 843
FEATURE                Location/Qualifiers
source                 1..843
                       mol_type = protein
                       organism = synthetic construct
SEQUENCE: 9
GERGAPGFRG PAGPNGIPGE KGPAGERGAP GERGAPGFRG PAGPNGIPGE KGPAGERGAP           60
GERGAPGFRG PAGPNGIPGE KGPAGERGAP GERGAPGFRG PAGPNGIPGE KGPAGERGAP          120
GERGAPGFRG PAGPNGIPGE KGPAGERGAP GERGAPGFRG PAGPNGIPGE KGPAGERGAP          180
GERGAPGFRG PAGPNGIPGE KGPAGERGAP GERGAPGFRG PAGPNGIPGE KGPAGERGAP          240
GERGAPGFRG PAGPNGIPGE KGPAGERGAP GERGAPGFRG PAGPNGIPGE KGPAGERGAP          300
GERGAPGFRG PAGPNGIPGE KGPAGERGAP GERGAPGFRG PAGPNGIPGE KGPAGERGAP          360
GERGAPGFRG PAGPNGIPGE KGPAGERGAP GERGAPGFRG PAGPNGIPGE KGPAGERGAP          420
GERGAPGFRG PAGPNGIPGE KGPAGERGAP GERGAPGFRG PAGPNGIPGE KGPAGERGAP          480
GAPGPCCGGG GGGSGGGGSG GGGSGGGGSD TICIGYHANN STDTVDTIFE KNVAVTHSVN          540
LLEDRHNGKL CKLKGIAPLQ LGKCNIIGWL LGNPECDSLL PARSWSYIVE TPNSENGACY          600
PGDFIDYEEL REQLSSVSSL ERFEIFPKES SWPNHTFNGV TASCSHRGKS SFYRNLLWLT          660
KKGDSYPKLT NSYVNNKGKE VLVLWGVHHP SSSDEQQSLY SNGNAYVSVA SSNYNRRFTP          720
EIAARPKVKD QHGRMNYYWT LLEPGDTIIF EATGNLIAPW YAFALSRGFE SGIITSNASM          780
HECNTKCQTP QGSINSNLPF QNIHPVTIGE CPKYVRSTKL RMVTGLRNIP SIQYRHHHHH          840
HHH                                                                       843

SEQ ID NO: 10          moltype = AA  length = 326
FEATURE                Location/Qualifiers
source                 1..326
                       mol_type = protein
                       organism = synthetic construct
SEQUENCE: 10
DTICIGYHAN NSTDTVDTIF EKNVAVTHSV NLLEDRHNGK LCKLKGIAPL QLGKCNIIGW           60
LLGNPECDSL LPARSWSYIV ETPNSENGAC YPGDFIDYEE LREQLSSVSS LERFEIFPKE          120
SSWPNHTFNG VTASCSHRGK SSFYRNLLWL TKKGDSYPKL TNSYVNNKGK EVLVLWGVHH          180
PSSSDEQQSL YSNGNAYVSV ASSNYNRRFT PEIAARPKVK DQHGRMNYYW TLLEPGDTII          240
FEATGNLIAP WYAFALSRGF ESGIITSNAS MHECNTKCQT PQGSINSNLP FQNIHPVTIG          300
ECPKYVRSTK LRMVTGLRNI PSIQYR                                              326
```